United States Patent
Chen et al.

(10) Patent No.: US 6,835,472 B2
(45) Date of Patent: Dec. 28, 2004

(54) ORGANIC ELECTROLUMINESCENT MATERIAL AND ORGANIC ELECTROLUMINESCENT DEVICE FABRICATED USING SAID MATERIAL

(75) Inventors: Ruey Min Chen, Tainan Science-Based Industrial Park (TW); Chun Che Hsu, Tainan Science-Based Industrial Park (TW); Jun Wen Chung, Tainan Science-Based Industrial Park (TW)

(73) Assignee: Chi Mei Optoelectronics Corp. (TW)

( * ) Notice: Subject to any disclaimer, the term of this patent is extended or adjusted under 35 U.S.C. 154(b) by 0 days.

(21) Appl. No.: 10/241,448

(22) Filed: Sep. 12, 2002

(65) Prior Publication Data

US 2003/0143425 A1 Jul. 31, 2003

(30) Foreign Application Priority Data

Jan. 29, 2002 (TW) ........................................ 91101617 A

(51) Int. Cl.[7] ........................ H05B 33/14; C07C 211/00
(52) U.S. Cl. ........................ 428/690; 428/917; 428/704; 313/504; 313/506; 252/301.16; 252/301.35; 564/426; 564/431; 564/433; 564/434
(58) Field of Search .................. 428/690, 917, 428/704; 313/504, 506; 252/301.16, 301.35; 564/426, 431, 433, 434

(56) References Cited

U.S. PATENT DOCUMENTS 5,858,563 A * 1/1999 Sano et al. ................. 428/690

5,935,720 A 8/1999 Chen et al.

OTHER PUBLICATIONS

Kim et al. (Design and synthesis of a novel red electroluminescent dye, Synthetic Metals 123 (1) p 43–46, published Aug. 22, 2001).*

* cited by examiner

Primary Examiner—Deborah Jones
Assistant Examiner—Ling Xu

(57) ABSTRACT

An organic material capable of generating luminescence by charge of an electric current includes a compound having a general formula (1):

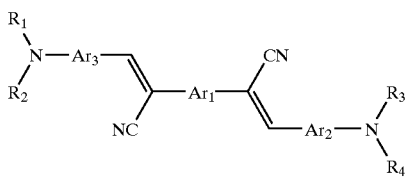

wherein $Ar_1$, $Ar_2$ and $Ar_3$ may be the same or different and, respectively, represent a substituted or unsubstituted aryl group or heterocyclic aryl group and wherein $R_1$, $R_2$, $R_3$, and $R_4$ may be the same or different and, respectively, represent a alkyl group, cycloalkyl group, a substituted or unsubstituted aryl group or heterocyclic aryl group.

14 Claims, 1 Drawing Sheet

ORGANIC ELECTROLUMINESCENT MATERIAL AND ORGANIC ELECTROLUMINESCENT DEVICE FABRICATED USING SAID MATERIAL

BACKGROUND OF THE INVENTION

1. Field of the Invention

This invention relates to an organic electroluminescent material and an organic electroluminescent device fabricated using the material. More specifically, the present invention relates to an organic luminescent material used for full color display and an organic electroluminescent device fabricated using the material.

2. Description of the Related Art

Electroluminescent devices using organic luminescent materials have been actively researched recently because of wider viewing angles and faster response time than conventional LCDs. More particularly, when using organic compounds as a luminescent material, it has been expected to realize a flat panel display, which makes use of spontaneous light and has a high response speed regardless of an angle of field. These organic electroluminescent devices when incorporated in consumer electronic devices such digital camera, PDA and videophones will offer several advantages such as low power consumption, high brightness, and light and thin design.

Typically, the organic electroluminescent (EL) device has an organic thin film which contains a luminescent material capable of emitting light through the charge of an electric current and is formed between an optically transparent anode and a metallic cathode. For the production of full-color EL display panel, it is necessary to have efficient red, green and blue (RGB) EL materials with proper chromaticity and sufficient luminance efficiency.

Currently, organic electroluminescent devices still have problems to solve. There has been difficulty in developing a stable red luminescent material with high luminance. For instance, red luminescent material DCJTB, disclosed in U.S. Pat. No. 5,935,720 is not satisfactory because its high molecular dipole moment causes self-quench and results in low luminance efficiency.

SUMMARY OF THE INVENTION

It is an object of the present invention to provide a red luminescent material and an organic electroluminescent device fabricated using the material.

To achieve the above listed and other objects, the present invention provides an organic material capable of generating luminescence by charge of an electric current. The organic material contains a compound represented by the following general formula (1):

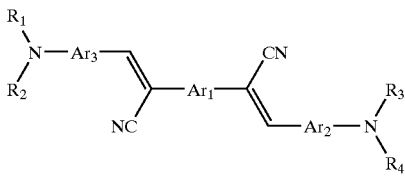

wherein $Ar_1$, $Ar_2$ and $Ar_3$ may be the same or different and, respectively, represent a substituted or unsubstituted aryl group or heterocyclic aryl group, and wherein $R_1$, $R_2$, $R_3$, and $R_4$ may be the same or different and, respectively, represent a alkyl group, cycloalkyl group, a substituted or unsubstituted aryl group or heterocyclic aryl group.

The compound represented by the general formula (1) and used as a luminescent material in the organic electroluminescent device of the invention may be available as at least one of the following structural formulas (2)-1 and (2)-2.

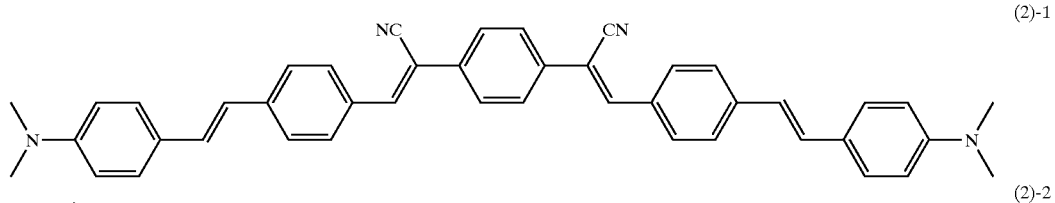

(2)-1

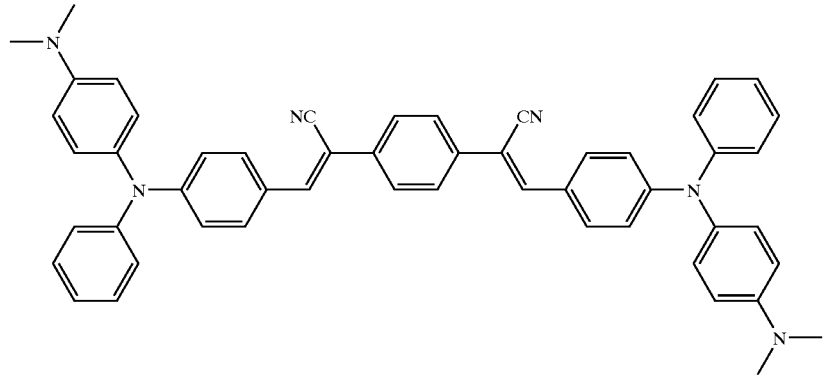

(2)-2

To achieve the above listed and other objects, the present invention further provides an organic electroluminescent device made of the compound represented by the general formula (1).

BRIEF DESCRIPTION OF THE DRAWINGS

Other objects, advantages, and novel features of the invention will become more apparent from the following detailed description when taken in conjunction with the accompanying drawings.

DETAILED DESCRIPTION OF THE PREFERRED EMBODIMENT

The present invention discloses a novel red luminescent material comprising a compound having a general formula (1):

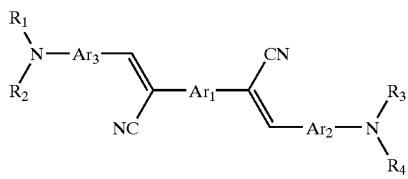

In the general formula (1), $Ar_1$, $Ar_2$ and $Ar_3$ may be the same or different and, respectively, represents an aryl group or a heterocyclic aryl group. The aryl group may be exemplified by a substituted or unsubstituted phenylene group, a substituted or unsubstituted naphthalene group, a substituted or unsubstituted anthracene group, a substituted or unsubstituted phenylene-vinylene group, a substituted or unsubstituted naphthalene-vinylene group, a substituted or unsubstituted anthracene-vinylene group, and a substitute or unsubstituted phenylene-vinylene-phenylene group. The heterocyclic aryl group may be exemplified by a substituted or unsubstituted thiophene group, a substituted or unsubstituted carbazole group, a substituted or unsubstituted pyrrole group, a substituted or unsubstituted pyridine group, a substituted or unsubstituted thiophene-vinylene group, a substituted or unsubstituted carbazole-vinylene group, and a substituted or unsubstituted pyrrole-vinylene group. $R_1$, $R_2$, $R_3$, and $R_4$ may be an alkyl group, a cycloalkyl group, or a substituted or unsubstituted aryl group or heterocyclic aryl group. The alkyl group may be exemplified by a methyl group, ethyl group, propyl group, isopropyl group, butyl group, isobutyl group and neobutyl group. The cycloalkyl group may be exemplified by a cyclopentyl group and cyclohexyl group. The substituted or unsubstituted aryl group may be exemplified by a substituted or unsubstituted phenylene group, a substituted or unsubstituted naphthalene group, and a substituted or unsubstituted anthracene group. The substituted or unsubstituted heterocyclic aryl group may be exemplified by a substituted or unsubstituted thiophene group, a substituted or unsubstituted carbazole group, and a substituted or unsubstituted pyrrole group.

The compound represented by the general formula (1) has both electron transportability and hole transportability, and can be used as a luminescent layer serving as an electron transport layer, or as a luminescent layer serving as a hole transport layer in an organic electroluminescent device. Moreover, it is possible to provide a device wherein the compound represented by the general formula (1) is formed as a luminescent layer sandwiched between an electron transport layer and a hole transport layer.

Figure 1:
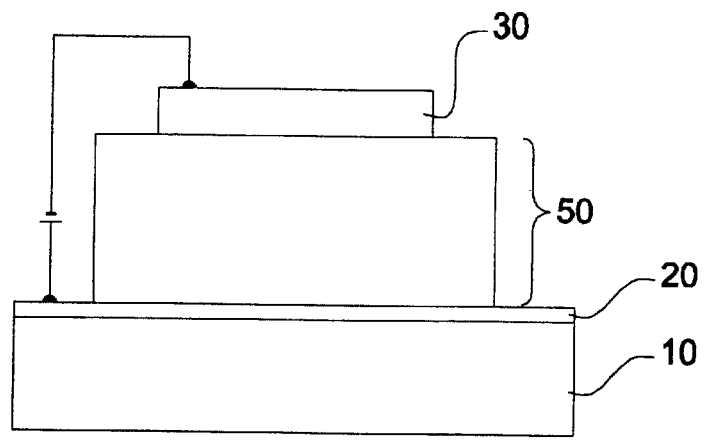
FIG. 1 is a schematic sectional view of an organic electroluminescent device according to one preferred embodiment of the invention.
Figure 2:
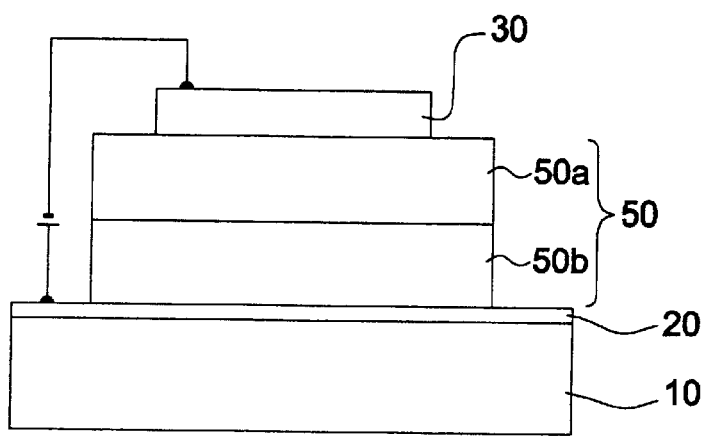
FIG. 2 is a schematic sectional view of an organic electroluminescent device according to another preferred embodiment of the invention.
Figure 3:
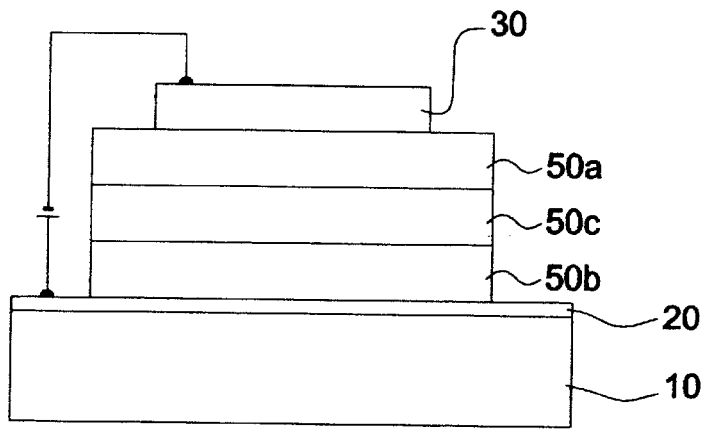
FIG. 3 is a schematic sectional view of an organic electroluminescent device according to still another preferred embodiment of the invention.

FIGS. 1 to 3 show embodiments of organic electroluminescent devices, respectively, according to the invention. In the figures, numeral 10 indicates a substrate for forming an organic electroluminescent device, which may be made of glass, plastics and other appropriate materials. Numeral 20 indicates a transparent electrode (anode), which can be made of ITO (indium tin oxide), $SnO_2$ or the like. Numeral 50 indicates an organic luminescent layer, which contains the above-mentioned compound represented by the general formula (1) as a luminescent material. The organic luminescent layer 50 may be formed on the upper surface of the anode 20 by physical vapor deposition (PVD) such as molecular beam deposition method, resistive heating method, and the like. Numeral 30 indicates a cathode formed by a metal thin film on the upper surface of the organic luminescent layer 50. The cathode may be made of an alloy or metal, such as, aluminum, magnesium, aluminum-lithium, magnesium-sliver, and the like.

In the organic electroluminescent device of the invention, the organic luminescent layer 50 may have an organic built-up structure. Referring to FIG. 2, the organic luminescent layer 50 includes an electron transport layer 50a, a hole transport layer 50b, and the compound represented by the general formula (1) may be contained in one or both of these layers to provide a luminescent electron transport layer 50a or hole transport layer 50b. Alternatively, for improving the luminescent performance, it is preferred to provide a structure (see FIG. 3) wherein the luminescent layer 50c containing the compound represented by the general formula (1) is sandwiched between the electron transport layer 50a and the hole transport layer 50b. The electron transport layer 50a may include tris(8-quinolinolat)aluminum ($Alq_3$), and the hole transport layer 50b may include Bis((N-(1-naphthyl-n-phenyl))benzidine (α-NPD).

The compound represented by the general formula (1) of the present invention can be synthesized through the synthetic sequences outlined in Scheme 1.

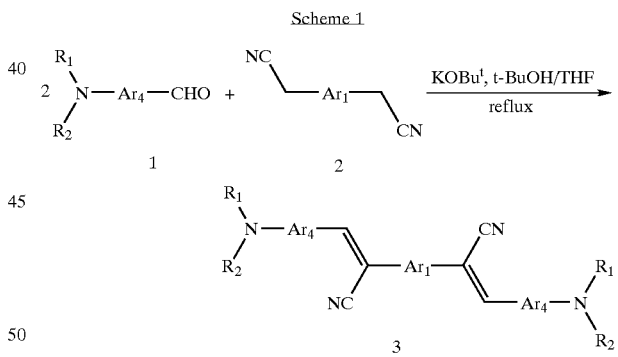

According to the synthetic sequences outlined in Scheme 1, 10 mmol of compound 1 and 5 mmol of compound 2 are added to a 100 ml reaction flask. 10 ml of t-BuOH and 10 ml of THF are then added as solvents, and the compounds are dissolved by stirring. Then, the solution is heated under reflux for 16 hours after 10 mmol of KOBu$^t$ is added. After reaction is complete, the solution is added dropwise to water so as to precipitate compound 3. Therefore, compound 3 is recovered as a solid product by suction filtration and is further purified through recrystallization using MeOH/$CH_2Cl_2$ as a solvent.

The compound represented by the general formula (1) of the invention can be also synthesized through the synthetic sequences outlined in Scheme 2.

Scheme 2

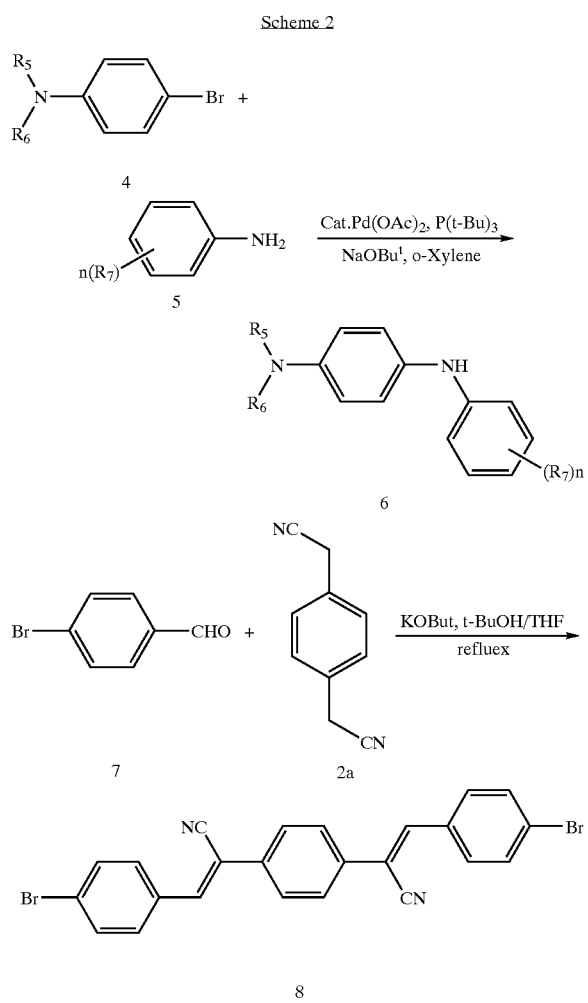

According to the synthetic sequences outlined in Scheme 2, 20 mmol of compound 4, 20 mmol of compound 5, and 20 mmol of NaOBu$^t$ are added to a 100 ml two-necked flask, and then 50 ml of o-xylene is added as a solvent. The compounds are dissolved by stirring. The solution is heated and refluxed for 24 hours after 1 mol % of Pd(OAc)$_2$ and 4 mol % of P(t-Bu)$_3$ are added as catalysts. The solvent is removed under reduced pressure and compound 6 is obtained by purification through column chromatography using acetic ester/n-hexane (1:10) as eluent.

Thereafter, 10 mmol of compound 7 and 5 mmol of compound 2a are added to a 100 ml flask. 10 ml of t-BuOH and 10 ml of THF are added as solvents. The compounds are dissolved by stirring. The solution is heated under reflux for 16 hours after 10 mmol of KOBu$^t$ is added. After reaction is complete, the solution is added dropwise to water so as to precipitate compound 8 which is recovered as the solid product by suction filtration and purified through sublimation under reduced pressure.

Finally, 10 mmol of compound 6, 5 mmol of compound 8, and 20 mmol of NaOBu$^t$ are added to a 100 ml two-necked flask, and 25 ml of o-xylene is added as a solvent. The reaction mixture is dissolved by stirring. The solution is heated under reflux for 24 hours after 1 mol % of Pd(OAc)$_2$ and 4 mol % of P(t-Bu)$_3$ is added as catalysts. When the solution cools down to room temperature, the solution is filtered and the filtrate is added to methanol so as to precipitate the solid product 9 which is obtained by suction filtration and purified through sublimation under reduced pressure.

EXAMPLES

The invention is more particularly described by way of examples, which should not be construed to limit the invention thereto.

Example 1

The compound represented by the structural formula (2)-1 is synthesized through the synthetic sequences outlined in Scheme 1.

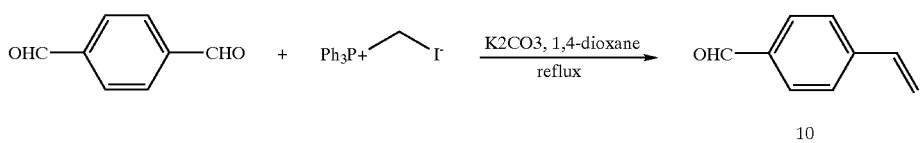

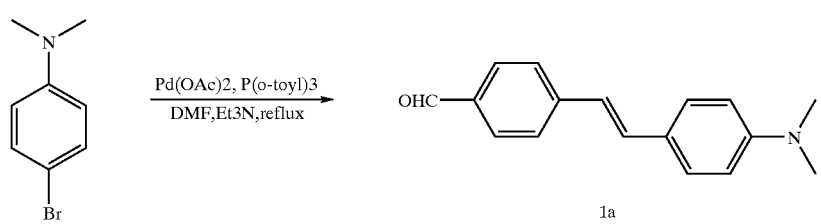

-continued

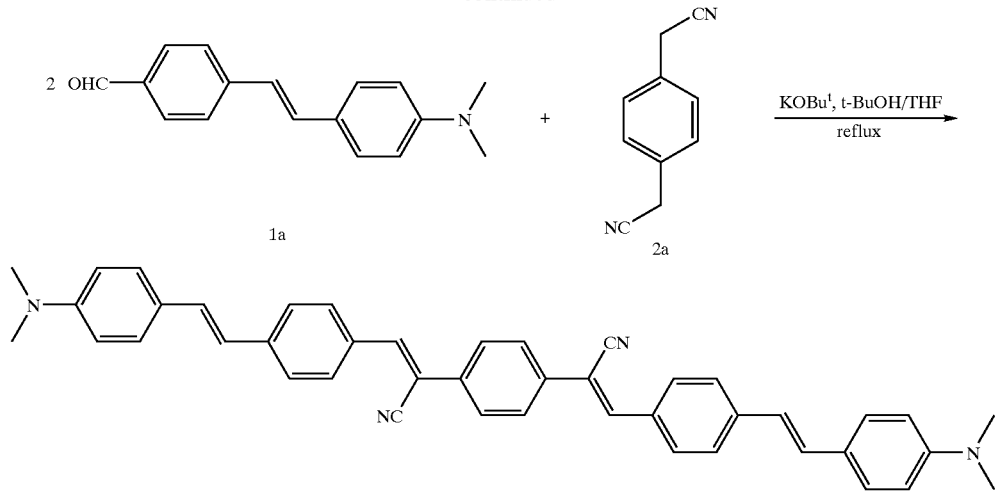

(1) First, 5.44 g (40 mmol) of terephthaldicarboxaldehyde is added to a 250 ml two-necked flask, and 100 ml of 1,4-dioxane and 1.5 ml of water are added as solvents. Then, the solution is heated under reflux for 24 hours after 16.2 g (40 mmol) of $Ph_3P^+CH_3I^-$ and 9.0 g of potassium carbonate are added. The solution is filtered to remove the solid therein and then the silica gel is added to the filtered solution. The solvent is removed under reduced pressure and compound 10 (2.64 g, yield=50%) is obtained by purification through column chromatography using 5% EA/Hexane as eluent.

(2) 3.96 g (30 mmol) of compound 10 and 6.06 g (30 mmol) of 4-Bromo-N, N-dimethylaniline are added to a 500 ml two-necked flask, and 150 ml of DMF and 90 ml of tri-ethyl amine are added as solvents. Then, the solution is heated for 24 hours under nitrogen atmosphere after 0.35 g (1.6 mmol) of $Pd(OAc)_2$ and 1.97 g (6.4 mmol) of $P(o\text{-toyl})_3$ are added as catalysts. The solution is added dropwise to water so as to precipitate the solid. Thereafter, yellow solid 1a (6.1 g, yield=81%) is obtained by suction filtration and purified through recrystallization using $MeOH/CH_2Cl_2$ as solvent.

(3) 2.51 g (10 mmol) of compound 1a ($Ar_4$ is phenylene-vinylene group) and 0.81 g (5 mmol) of compound 2a (p-phenylene-diacetonitrile ($Ar_1$ is phenyl group)) are added to a 100 ml two-necked flask, and 10 ml of t-BuOH and 10 ml of THF are added as solvents. Then, the solution is heated under reflux for 16 hours. After reaction is complete, the solution is added dropwise to water so as to precipitate the compound represented by the structural formula (2)-1. The solid product 3a is obtained by suction filtration and purified through recrystallization using $MeOH/CH_2Cl_2$ as solvent (yield=80%). The compound represented by the structural formula (2)-1 in $CHCl_3$ solution has a PL $\lambda max=593$ nm measured by fluorescent spectrometer.

Example 2

The compound represented by the structural formula (2)-2 is synthesized through the synthetic sequences outlined in Scheme 2.

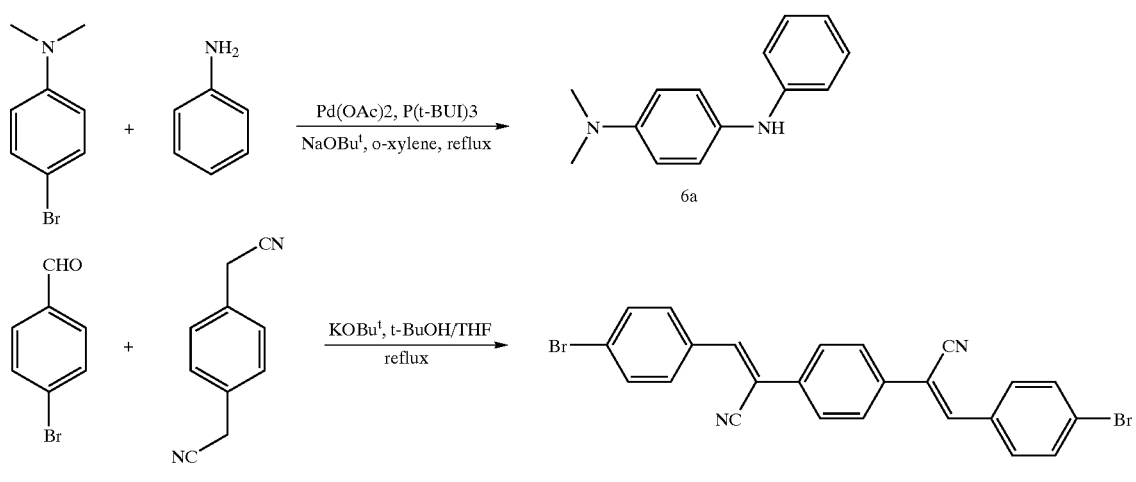

-continued

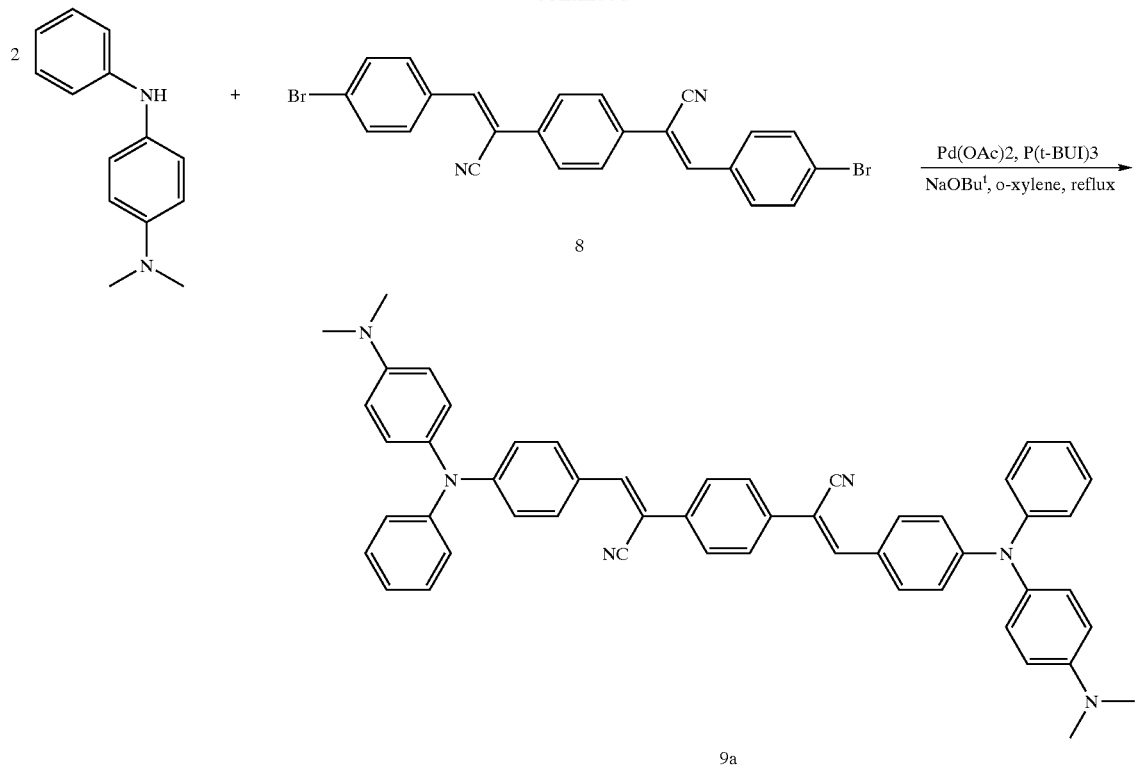

(1) First, 4.04 g (20 mmol) of 4-Bromo-N, N-dimethylaniline ($R_5$, $R_6$ are hydrogen), 1.86 g (20 mmol) of aniline ($R_7$ is hydrogen) and 1.92 g (20 mmol) of NaOBu$^t$ are added to a 100 ml two-necked flask and 50 mL of o-xylene is added as solvent. The reaction mixture is dissolved by stirring. Then, the solution is heated under reflux for 24 hours after 44 mg (1 mol %) of Pd(OAc)$_2$ and 0.16 g (4 mol %) of P(t-Bu)$_3$ are added as catalyst. The solvent is removed under reduced pressure and compound 6a is obtained by purification through column chromatography using acetic ester/n-hexane (1:10) as eluent (yield=50%).

(2) Then, 1.86 g (10 mmol) of 4-bromobenzaldehyde and 0.81 g (5 mmol) of compound 2a are added to a 100 ml two-necked flask, and 10 ml of t-BuOH and 10 ml of THF are added as solvents. The reaction mixture is dissolved by stirring. Then, the solution is heated under reflux for 16 hours after 1.2 g (10 mmol) of KOBu$^t$ is added. After reaction is complete, the solution is added dropwise to water so as to precipitate compound 8 which is recovered as the solid product by suction filtration and purified through sublimation under reduced pressure (yield=72%).

(3) Finally, 2.12 g (10 mmol) of compound 6a, 2.45 g (5 mmol) of compound 8 and 2.4 g (20 mmol) of NaOBu$^t$ are added to a 100 ml two-necked flask. 25 ml of o-xylene is added as solvent. The reaction mixture is dissolved by stirring. Then the reaction mixture is heated under reflux for 24 hours after 22 mg (1 mol %) of Pd (OAc)$_2$ and 80 mg (4 mol %) of P(t-Bu)$_3$ are added as catalysts. When the solution cools down to room temperature, the solution is filtered and the filtrate is added to methanol so as to precipitate the solid product 9a (represented by the structural formula (2)-2 which is obtained by suction filtration and purified through sublimation under reduced pressure (yield=75%). The compound represented by the structural formula (2)-1 in CHCl$_3$ solution has a PL λmax=593 nm measured by fluorescent spectrometer.

Although the invention has been explained in relation to its preferred embodiment, it is to be understood that many other possible modifications and variations can be made without departing from the spirit and scope of the invention as hereinafter claimed.

What is claimed is:

1. An organic luminescent material comprising a compound having a general formula (1):

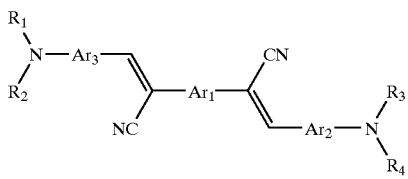

wherein:
Ar$_1$, Ar$_2$ and Ar$_3$, which can be the same or different and represent heterocyclic aryl group or a substituent selected from the group consisting of a substituted or unsubstituted naphthalene group, a substituted or unsubstituted anthracene group, a substituted or unsubstituted phenylene-vinylene group, a substituted or unsubstituted naphthalene-vinylene group, a substituted or unsubstituted anthracene-vinylene group, and a substituted or unsubstituted phenylene-vinylene-phenylene group; and R$_1$, R$_2$, R$_3$, and R$_4$ are selected from the group consisting of an alkyl group, a cycloalkyl group, an aryl group and a heterocyclic aryl group.

2. The organic luminescent material as claimed in claim 1, wherein the heterocyclic aryl group is selected from the group consisting of a substituted or unsubstituted thiophene group, a substituted or unsubstituted carbazole group, a substituted or unsubstituted pyrrole group, and a substituted or unsubstituted pyridine group.

3. The organic luminescent material as claimed in claim 1, wherein the heterocyclic aryl group is selected from the group consisting of a substituted or unsubstituted thiophene-vinylene group, a substituted or unsubstituted carbazole-vinylene group, and a substituted or unsubstituted pyrrole-vinylene group.

4. The organic luminescent material as claimed in claim 1, wherein the alkyl group is selected from the group consisting of methyl group, ethyl group, propyl group, isopropyl group, butyl group, isobutyl group, and neobutyl group; the cycloalkyl group is selected from the group consisting of cyclopentyl group and cyclohexyl group; the aryl group is selected from the group consisting of a substituted or unsubstituted phenylene group, a substituted or unsubstituted naphthalene group, and a substituted or unsubstituted anthracene group; and the heterocyclic aryl group is selected from the group consisting of a substituted or unsubstituted thiophene group, a substituted or unsubstituted carbazole group and a substituted or unsubstituted pyrrole group.

5. The organic luminescent material as claimed in claim 1, wherein R1, R2, R3, and R4 are selected from the group consisting of a substituted or unsubstituted phenylene group, a substituted or unsubstituted naphthalene group, a substituted or unsubstituted anthracene group, a substituted or unsubstituted thiophene group, a substituted or unsubstituted carbazole group, and a substituted or unsubstituted pyrrole group.

6. An organic electroluminescent device, comprising:
an anode and a cathode, and
an organic layer having a luminescent region and disposed between the anode and the cathode,
wherein the organic layer comprises an organic luminescent material as claimed in claim 1.

7. The organic electroluminescent device as claimed in claim 6, wherein the organic layer comprises an electron transport layer and a hole transport layer, wherein the hole transport layer comprises an organic luminescent material represented by the general formula (1).

8. The organic electroluminescent device as claimed in claim 6, wherein the organic layer comprises a hole transport layer and an electron transport layer, wherein the electron transport layer comprises an organic luminescent material represented by the general formula (1).

9. The organic electroluminescent device as claimed in claim 6, wherein the organic layer comprises a hole transport layer, a luminescent layer and an electron transport layer, wherein the luminescent layer comprises an organic luminescent material represented by the general formula (1).

10. An organic luminescent material comprising a compound represented by a structural formula as follows

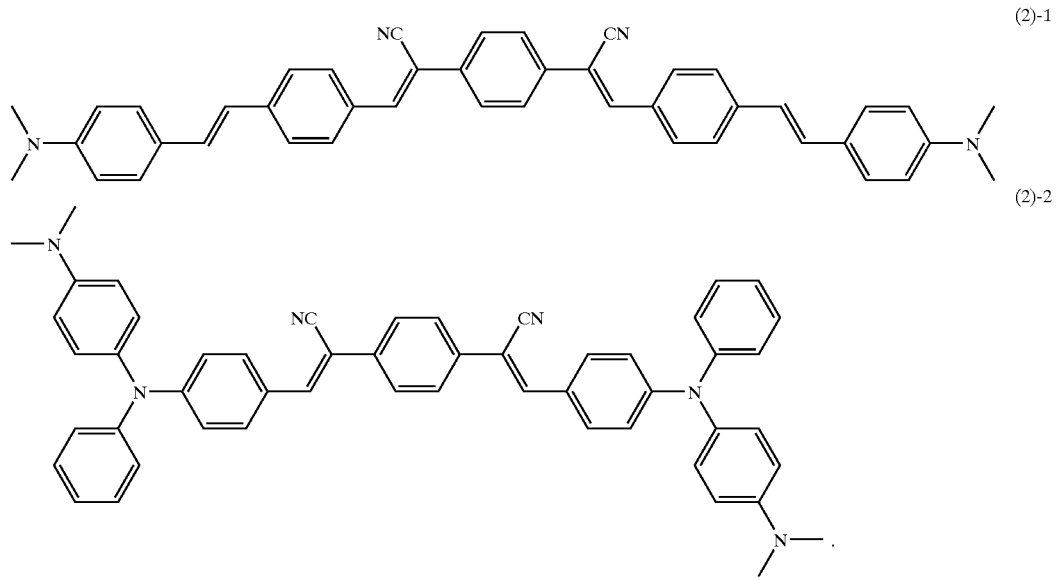

11. An organic electroluminescent device, comprising:
an anode and a cathode, and
an organic layer having a luminescent region and disposed between the anode and the cathode,
wherein the organic layer comprises an organic luminescent material as claimed in claim 10.

12. The organic electroluminescent device as claimed in claim 11, wherein the organic layer comprises an electron transport layer and a hole transport layer, wherein the hole transport layer comprises an organic luminescent material represented by the structural formula (2)-1 or the structural formula (2)-2 in claim 10.

13. The organic electroluminescent device as claimed in claim 11, wherein the organic layer comprises a hole transport layer and an electron transport layer, wherein the electron transport layer comprises an organic luminescent material represented by the structural formula (2)-1 or the structural formula (2)-2 in claim 10.

14. The organic electroluminescent device as claimed in claim 11, wherein the organic layer comprises a hole transport layer, a luminescent layer and an electron transport layer, wherein the luminescent layer comprises an organic luminescent material represented by the structural formula (2)-1 or the structural formula (2)-2 in claim 10.

* * * * *

UNITED STATES PATENT AND TRADEMARK OFFICE
CERTIFICATE OF CORRECTION

PATENT NO.         : 6,835,472 B2
APPLICATION NO. : 10/241448
DATED                : December 28, 2004
INVENTOR(S)      : Ruey-Min Chen et al.

Page 1 of 1

It is certified that error appears in the above-identified patent and that said Letters Patent is hereby corrected as shown below:

Item [73] Assignee should read -- Chi Mei Optoelectronics Corp. and Kyocera Corporation --

Signed and Sealed this

Second Day of June, 2009

JOHN DOLL
*Acting Director of the United States Patent and Trademark Office*